US005882856A

United States Patent [19]

Shuber

[11] Patent Number: 5,882,856
[45] Date of Patent: Mar. 16, 1999

[54] UNIVERSAL PRIMER SEQUENCE FOR MULTIPLEX DNA AMPLIFICATION

[75] Inventor: Anthony P. Shuber, Millford, Mass.

[73] Assignee: Genzyme Corporation, Framingham, Mass.

[21] Appl. No.: 474,450

[22] Filed: Jun. 7, 1995

[51] Int. Cl.[6] .......................... C12P 19/34; C07H 21/04; C12Q 1/68

[52] U.S. Cl. ........................... 435/6; 435/91.1; 435/51.2; 536/243

[58] Field of Search .......................... 536/24.3; 435/91.2, 435/91.1, 6

[56] References Cited

U.S. PATENT DOCUMENTS 5,104,792  4/1992  Silver et al. .................................. 435/6

FOREIGN PATENT DOCUMENTS

| 0 682 640 A1 | 12/1994 | European Pat. Off. . |
| WO 93/18177 | 9/1993 | WIPO . |
| WO 93/18178 | 9/1993 | WIPO . |

OTHER PUBLICATIONS

E. Berg et al., "Hybrid PCR Sequencing: Sequencing a Universal Primer", *Biotechniques*, 17,5: 896–901 (1994).
T. Chenhui, "Program for Estimating the Melting Temperature and the Guanine Plus Cytosine Content of DNA", *The Journal of Heredity*, 84, 3:236–237 (1993).
A. Chetverin, "Oligonucleotide Arrays: New Concepts and Possibilities", Bio/Technology, 12:1093–1099 (1994).
S. Ebrahimi et al., "Studies of the Interaction of a meta–Hydroxy AnaloguHoechst 33258 with DNA by Melting Temperature, Footprinting and High–resolution [1] H NMR Spectroscopy", *J Chem. Soc. Chem. Commun.*, 1398–1399, (1992).
M. Edwards et al., "Multiplex PCR: Advantages, Development and Applications", *PCR Methods and Applications*, 3:565–575 (1994).
Y. Feng et al., "Criterion for DNA melting in the mean–field modified self–consistent phonon theory", *Physical Review B*, 43, 11:9284–9286, (1991).
Y. Feng et al., "Modified self–consistent phonon calculation of the dependence of DNA melting temperature on guanine–cytosine content", 46,12:8002–8006 (1992).
T. Hung et al. "A specificty enhancer for polymerase chain reaction", *Nucleic Acids Research*, 18, 16:4953 (1990).
H. Ide et al., "On the mechanism of preferential incorporation of dAMP at abasic sites in translesional DNA synthesis. Role of proofreading activity of DNA polymerase and thermodynamic characterization of model template–primers containing an abasic site", *Nucleic Acids Research*, 23,1:123–129 (1995).
G. Kumar et al., "DNA Polymorphism Under the Influence of Low pH and Low Temperature",*Journal of Biomolecular Structure & Dynamics*, 12,1:183–201 (1994).
W. Melchoir et al., "Alternation of the Relative Stability of dA·dT and dG·dC Base Pairs in DNA", *Proc. Nat. Acad. Sci. USA*, 70,2:298–302 (1973).

A. Moreau et al., "Improvement of GC–Rich Template Amplification by Inverse PCR", *Bio Techniques*, 17, 2:233–234 (1994).
S. Morse et al., "Purine–purine mismatches in RNA helices: evidence for protonated G·A pairs and next–nearest neighbor effects", *Nucleic Acids Research*, 23, 2:302–306 (1995).
G. Mutter et al., "PCR bias in amplification of androgen receptor alleles, a trinucleotide repeat marker used in clonality studies", *Nucleic Acids Research*, 23, 8:1411–11418 (1995).
P. Ponnuswamy et al., "On the Conformational Stability of Oligonucleotide Duplexes and tRNA Molecules", *J. theor. Biol.*, 169:419–432 (1994).
B. Peral et al., "Evidence of Linkage Disequilibrium in the Spanish Polycystic Kidney Disease I Populatin"*Am J. Hum. Genet..*, 54:899–908 (1994).
M. Peyrard et al., "Dynamics of DNA 'Melting'", *Nanobiology*, I:313–324 (1992).
M. Record, Jr. et al., "Theoretical Studies of the Thermodynamic Consequences of Interactions of Ions with Polymeric and Oligomeric DNA: The Preferential Interaction Coefficient and Its Application to the Termodynamic Analysis of Elecvtrolyte Effects on Conformational Stability and Ligand Binding", *Theoretical Biochemistry & Molecular Biophysics*, 28, 4:285–307 (1990).
A. Orou et al., "Automatic separation of two PCRs in one tube by annealing temperature", *Tr. Genetics*, 11, 4:127–128 (1995).
W. Rychlik, "Priming Efficiency in PCR", *BioTechniques*, 18, 1:84–90 (1995).
A. Shuber et al., "A Simplified Procedure for Developing Multiplex PCRs" *Genome Research*, 5:488–498 (1995).
K. Sugimoto et al., "A Rapid Isolation of the Unknown 5"–Flanking Sequence of Human CENP–B cDNA withPolymerase Chain Reactions", *Agric. Biol. Chem.*, 55, 11:2687–2692 (1991).
N. Sugimoto et al., "Thermodynamic Parameters To Predict Stability of RNA/DNA Hybrid Duplexes", *Biochemistry*, 34:11211–11216 (1995).
T. Sugimoto et al., "Quantitative Detection of DNA by Coamplification Polymerase Chain Reaction: A Wide Detectable Range controlled by the Thermodynamic Stability of Primer Template Duplexes",*Analytical Biochemistry*, 211:170–172 (1993).

(List continued on next page.)

*Primary Examiner*—Kenneth R. Horlick
*Assistant Examiner*—Joyce Tung
*Attorney, Agent, or Firm*—Rae-Venter Law Group, P.C.

[57] ABSTRACT

The present invention provides primers that allow simultaneous amplification of multiple DNA target sequences present in a DNA sample. Further provided are methods for detecting multiple defined target DNA sequences in a DNA sample. Methods for high-throughput genetic screening are also provided. In yet another aspect, the present invention provides single-stranded oligonucleotide DNA primers for amplification of a target DNA sequence in a multiplex polymerase chain reaction.

18 Claims, 6 Drawing Sheets

OTHER PUBLICATIONS

M. Tuliszka et al., "A new method of investigation of DNA melting process—the thermal conductivity method" *Thermochimica Acta,* 194:67–75 (1992).

S. Turner et al., "Use of Deoxyinosine in PCR to Improve Amplification of GC–Rich DNA", *Biotechniques,* 19,1 (1995).

R. Wallace et al., "Hybridization of synthetic oligodeoxyribonucleotides to Φχ 174 DNA: the effect of single base pair mismatch" *Nucleic Acids Research,* 6, 11:3543–3557 (1979).

F. Weighardt et al., "A Simple Procedure for Enhancing PCR Specificity", *PCR Methods and Applications,* 3:77–80 (1993).

R. Varanasi et al., "Fine structure analysis of the WT1 gene in sporadic Wilms tumors", *Proc. Natl. Acad. Sci. USA,* 91:3554–3558 (1994).

J. Guatelli, et al., "Nucleic Acid Amplification In Vitro: Detection of Sequences with Low Copy Numbers and Application to Diagnosis of Human Immunodeficiency Virus Type 1 Infection", *Clinical Microbiology Reviews,* 2(2):217–226 (1989).

A. Jeffreys, et al., "Minisatellite repeat coding as a digital approach to DNA typing", *Nature,* 354:204–209 (1991).

S.T. Jones, et al., "Rapid PCR–Cloning of Full–Length Mouse Immunoglobulin Variable Regions", *Bio/Technology,* 9:88–89 (1991).

Picci et al. Screening for cystic fibrosis gene mutations by multiplex DNA amplification. Hnm. Genet. 1992, vol. 88, pp. 552–556.

Weighardt et al. A Simple Procedure for Enhancing PCR Specificity, 1993, vol. 3 pp. 77–80.

| SEQ IDNO: | Cystic Fibrosis Transmembrane Regulator(CFTR) 15-plex Primer Sequences | Exon | Size (bp) | SEQ IDNO: | Gauchers(GCR) and Sickle Cell Anemia(SCA) 4-plex GCR Primer Sequences | Exon | Size (bp) |
|---|---|---|---|---|---|---|---|
| 1 | AGG CTT CTC AGT GAT CTG TTG | Int 19 | ~440 | 37 | GGG TGG GAG GGT GGA AAG GGC TAA TGG | 6 | 401 |
| 2 | GAA TCA TTC AGT GGG TAT AAG CAG | | | 38 | CCA GAA GGT AGA AAG GTG AG | | 358 |
| 3 | GCC CGA CAA ATA ACC AAG TGA | 19 | 410 | 39 | GAA TGT CCC AAG CCT TTG A | 2 | |
| 4 | AGT CTA ACA AGT CAA GCA GTG | | | 40 | AAG CTG AAG CAA GAG AAT CG | | |
| 5 | TGA TGG TAA GTA CAT GGG TG | 21 | 381 | 41 | TGC AAC TAC TGA GGC ACT T | 9 | 319 |
| 6 | CAA AAG TAC CTG TTG CTC CA | | | 42 | TAC AAT GAT GGG ACT GTC G | | |
| 7 | CTT CTA ATG GTG ATG ACA GCC T | 9 | 335 | | SCA Primer Sequences | | |
| 8 | CCA CTG AAA ATA TGA GGA AAT | | | 43 | CAT TTG CTT CTG ACA CAA CTG | | 124 |
| 9 | AGG TAG CAG CTA TTT TTG TTA TGG | 13 | 295 | 44 | CCA ACT TCA TCC ACG TTC ACC | | |
| 10 | TAA GGG AGT CTT TTG CAC AA | | | | GCR and Tay-Sachs (TS) 3-plex | | |
| | | | | | GCR | | |
| 11 | TGT AGG AAG TCA CCA AAG | 4 | 267 | 45 | CCT TGC CCT GAA CCC CGA A | 9, 10, 11 | 871 |
| 12 | CGA TAC AGA ATA TAT GTG CC | | | 46 | CTG ACT CTG TCC CTT TAA TGC CCA | | |
| 13 | GGA GTC CAA TTT TCA CTC ATC TTG T | 17b | 245 | 47 | TS Primer Sequences | | |
| | | | | | GTG TGG CGA GAG GAT ATT CCA | 11, 12*** | 530 |
| 14 | AGT TAA TGA GTT CAT AGT ACC TGT T | | | 48 | TGG CTA GAT GGG ATT GGG TCT | | |
| 15 | AGA TAC GTC AAT AGC TCA GCC | 7 | 220 | 49 | GGG TCC TAC AAC CCT GTC ACC CAC | 7*** | 190 |
| 16 | GGT ACA TTA CCT GTA TTT TGT TT | | | 50 | AAG CTT CAC TCT GAG CAT AAC AAG | | |
| 17 | CAG ATT GAG CAT ACT AAA AGT G | 11 | 200 | | B-thalassemia Primer Sequences | | |
| 18 | TAC ATG AAT GAC ATT TAC AGC A | | | 51 | GCT GTC ATC ACT TAG ACC TC | 1, 2, 3 | 1612 |
| 19 | GAG CCT TCA GAG GGT AAA AT | 10 | 175 | 52 | GCA AGA AAG CGA GCT TAG TG | | |
| 20 | TCA CAT AGT TTC TTA CCT CT | | | | | | |

FIG. 1A

| SEQ IDNO: | Primer Sequences | Exon | Size (bp) |
|---|---|---|---|
| 21 22 | AAG AAC TGG ATC AGG GAA GA / TCC TTT TGC TCA CCT GTG GT | 20 | 155 |
| 23 24 | GCT GTC AAG CCG TGT TCT A / GTA TAA TTT ATA ACA ATA GTG CC | 5 | 132 |
| 25 26 | TTG GTT GTG CTG TGG CTC CT / ACA ATA CAT ACA AAC ATA GTG G | 14b | 110 |
| 27 28 | GAC TCT CCT TTT GGA TAC CTA / GCA TGA GCA TTA TAA GTA AGG | 12 | 90 |
| 29 30 | GGC GAT GTT TTT TCT GGA GA / ACA AAT GAG ATC CTT ACC CC | 3 | 70 |

CFTR Exon 21 Primer Sequences

| SEQ IDNO: | Primer Sequences |
|---|---|
| 31 32 | CAA GTG AAT CCT GAG CGT GAT TT / CAA AAG TAC CTG TTG CTC CA |
| 33 34 | GAA CTT GAT GGT AAG TAC ATG GGT G / AGT CAA AAG TAC CTG TTG CTC CAG |
| 35 36 | TGA TGG TAA GTA CAT GGG TG / CAA AAG TAC CTG TTG CTC CA |

| SEQ IDNO: | WT-1 Primer Sequences | Name | Size (bp) |
|---|---|---|---|
| 53 54 | CTG AGT GAA TGG AGC GGC / GGG TGA ATG AGT AGG TGG | B* | 204 |
| 55 56 | CGG TGC TGG ACT TTG CG / AAG TGG ACA GTG AAG GCG | F | 186 |
| 57 58 | CCG TCT TGC GAG AGC ACC / CTA ATT TGC GGG TTA GG | H* | 262 |
| 59 60 | AGT TGT GTA TAT TTG TGG TTA TG / GTT ACT GTG GAA AGG CAA TG | J | 167 |
| 61 62 | GAG ATC CCC TTT TCC AG / CAC AGC TGC CAG CAA TG | N* | 176 |
| 63 64 | CTC ACT GTG CCC ACA TTG / CAA TTT CAT TCC ACA ATA G | O* | 211 |

| Name | Size (bp) |
|---|---|
| SS#1 | 477 |
| SS#2 | 389 |
| SS#3 | 381 |

\* Reported previously by Varanasi et al 1994.
\*\* Reported previously by Navon & Proia 1989.
\*\*\* Reported previously by Tanaka et al 1990.

NOTE:
Amplicon sizes increase by 40bp for chimeric primers.

FIG. 1B

SEQUENCE LISTING ( 1 ) GENERAL INFORMATION:

( i i i ) NUMBER OF SEQUENCES: 65

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "CFTR 15-PLEX PRIMER SEQUENCE - int19"

( x i ) SEQUENCE DESCRIPTION: SEQ ID NO:1:

A G G C T T C T C A     G T G A T C T G T T     G     2 1

( 2 ) INFORMATION FOR SEQ ID NO:2:

( i ) SEQUENCE CHARACTERISTICS:
        ( A ) LENGTH: 24 base pairs ( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "CFTR 15-PLEX PRIMER
SEQUENCE - int19"

( x i ) SEQUENCE DESCRIPTION: SEQ ID NO:2:

GAATCATTCA GTGGGTATAA GCAG 24

( 2 ) INFORMATION FOR SEQ ID NO:3:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "CFTR 15-PLEX PRIMER
SEQUENCE - exon 19"

( x i ) SEQUENCE DESCRIPTION: SEQ ID NO:3:

GCCCGACAAA TAACCAAGTG A 21

( 2 ) INFORMATION FOR SEQ ID NO:4:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "CFTR 15-PLEX PRIMER
SEQUENCE - exon 19"

( x i ) SEQUENCE DESCRIPTION: SEQ ID NO:4:

AGTCTAACAA AGCAAGCAGT G 21

( 2 ) INFORMATION FOR SEQ ID NO:5:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "CFTR 15-PLEX PRIMER
SEQUENCE - exon 21"

( x i ) SEQUENCE DESCRIPTION: SEQ ID NO:5:

TGATGGTAAG TACATGGGTG 20

( 2 ) INFORMATION FOR SEQ ID NO:6:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "CFTR 15-PLEX PRIMER
SEQUENCE - exon 21"

( x i ) SEQUENCE DESCRIPTION: SEQ ID NO:6:

CAAAAGTACC TGTTGCTCCA 20

( 2 ) INFORMATION FOR SEQ ID NO:7:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "CFTR 15-PLEX PRIMER
            SEQUENCE - exon 9"

( x i ) SEQUENCE DESCRIPTION: SEQ ID NO:7:

CTTCTAATGG TGATGACAGC CT                                      22

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "CFTR 15-PLEX PRIMER
            SEQUENCE - exon 9"

( x i ) SEQUENCE DESCRIPTION: SEQ ID NO:8:

CCACTGAAAA TAATATGAGG AAAT                                    24

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "CFTR 15-PLEX PRIMER
            SEQUENCE - exon 13"

( x i ) SEQUENCE DESCRIPTION: SEQ ID NO:9:

AGGTAGCAGC TATTTTTATG G                                        21

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "CFTR 15-PLEX PRIMER
            SEQUENCE - exon 13"

( x i ) SEQUENCE DESCRIPTION: SEQ ID NO:10:

TAAGGGAGTC TTTTGCACAA                                          20

( 2 ) INFORMATION FOR SEQ ID NO:11:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "CFTR 15-PLEX PRIMER
            SEQUENCE - exon 4"

( x i ) SEQUENCE DESCRIPTION: SEQ ID NO:11:

TGTAGGAAGT CACCAAAG  18

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "CFTR 15-PLEX PRIMER
            SEQUENCE - exon 4"

( x i ) SEQUENCE DESCRIPTION: SEQ ID NO:12:

CGATACAGAA TATATGTGCC  20

( 2 ) INFORMATION FOR SEQ ID NO:13:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "CFTR 15-PLEX PRIMER
            SEQUENCE - exon 17b"

( x i ) SEQUENCE DESCRIPTION: SEQ ID NO:13:

GGAGTCCAAT TTTCACTCAT CTTG  24

( 2 ) INFORMATION FOR SEQ ID NO:14:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "CFTR 15-PLEX PRIMER
            SEQUENCE - exon 17b"

( x i ) SEQUENCE DESCRIPTION: SEQ ID NO:14:

AGTTAATGAG TTCATAGTAC CTGTT  25

( 2 ) INFORMATION FOR SEQ ID NO:15:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "CFTR 15-PLEX PRIMER
            SEQUENCE - exon 7"

( x i ) SEQUENCE DESCRIPTION: SEQ ID NO:15:

AGATACTTCA ATAGCTCAGC C  21

( 2 ) INFORMATION FOR SEQ ID NO:16:

( i ) SEQUENCE CHARACTERISTICS:
        ( A ) LENGTH: 23 base pairs
        ( B ) TYPE: nucleic acid
        ( C ) STRANDEDNESS: single ( D ) TOPOLOGY: linear ( i i ) MOLECULE TYPE: other nucleic acid
    ( A ) DESCRIPTION: /desc = "CFTR 15-PLEX PRIMER
        SEQUENCE - exon 7"

( x i ) SEQUENCE DESCRIPTION: SEQ ID NO:16:

GGTACATTAC CTGTATTTTG TTT                    23

( 2 ) INFORMATION FOR SEQ ID NO:17:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "CFTR 15-PLEX PRIMER
            SEQUENCE - exon 11"

( x i ) SEQUENCE DESCRIPTION: SEQ ID NO:17:

CAGATTGAGC ATACTAAAAG TG                    22

( 2 ) INFORMATION FOR SEQ ID NO:18:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "CFTR 15-PLEX PRIMER
            SEQUENCE - exon 11"

( x i ) SEQUENCE DESCRIPTION: SEQ ID NO:18:

TACATGAATG ACATTTACAG CA                    22

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "CFTR 15-PLEX PRIMER
            SEQUENCE - exon 10"

( x i ) SEQUENCE DESCRIPTION: SEQ ID NO:19:

GAGCCTTCAG AGGGTAAAAT                      20

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "CFTR 15-PLEX PRIMER
            SEQUENCE - exon 10"

( x i ) SEQUENCE DESCRIPTION: SEQ ID NO:20:

TCACATAGTT TCTTACCTCT                      20

( 2 ) INFORMATION FOR SEQ ID NO:21:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "CFTR 15-PLEX PRIMER SEQUENCE - exon 20"

( x i ) SEQUENCE DESCRIPTION: SEQ ID NO:21:

AAGAACTGGA TCAGGGAAGA     20

( 2 ) INFORMATION FOR SEQ ID NO:22:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "CFTR 15-PLEX PRIMER SEQUENCE - exon 20"

( x i ) SEQUENCE DESCRIPTION: SEQ ID NO:22:

TCCTTTTGCT CACCTGTGGT     20

( 2 ) INFORMATION FOR SEQ ID NO:23:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "CFTR 15-PLEX PRIMER SEQUENCE - exon 5"

( x i ) SEQUENCE DESCRIPTION: SEQ ID NO:23:

GCTGTCAAGC CGTGTTCTA     19

( 2 ) INFORMATION FOR SEQ ID NO:24:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "CFTR 15-PLEX PRIMER SEQUENCE - exon 5"

( x i ) SEQUENCE DESCRIPTION: SEQ ID NO:24:

GTATAATTTA TAACAATAGT GCC     23

( 2 ) INFORMATION FOR SEQ ID NO:25:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "CFTR 15-PLEX PRIMER SEQUENCE - exon 14b"

( x i ) SEQUENCE DESCRIPTION: SEQ ID NO:25:

TTGGTTGTGC TGTGGCTCCT 20

( 2 ) INFORMATION FOR SEQ ID NO:26:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "CFTR 15-PLEX PRIMER SEQUENCE - exon 14b"

( x i ) SEQUENCE DESCRIPTION: SEQ ID NO:26:

ACAATACATA CAAACATAGT GG 22

( 2 ) INFORMATION FOR SEQ ID NO:27:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "CFTR 15-PLEX PRIMER SEQUENCE - exon 12"

( x i ) SEQUENCE DESCRIPTION: SEQ ID NO:27:

GACTCTCCTT TTGGATACCT A 21

( 2 ) INFORMATION FOR SEQ ID NO:28:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "CFTR 15-PLEX PRIMER SEQUENCE - exon 12"

( x i ) SEQUENCE DESCRIPTION: SEQ ID NO:28:

GCATGAGCAT TATAAGTAAG G 21

( 2 ) INFORMATION FOR SEQ ID NO:29:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "CFTR 15-PLEX PRIMER SEQUENCE - exon 3"

( x i ) SEQUENCE DESCRIPTION: SEQ ID NO:29:

GGCGATGTTT TTTCTGGAGA 20

( 2 ) INFORMATION FOR SEQ ID NO:30:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear (i i) MOLECULE TYPE: other nucleic acid
(A) DESCRIPTION: /desc = "CFTR 15-PLEX PRIMER
SEQUENCE - exon 3"

(x i) SEQUENCE DESCRIPTION: SEQ ID NO:30:

ACAAATGAGA TCCTTACCCC    20

(2) INFORMATION FOR SEQ ID NO:31:

(i) SEQUENCE CHARACTERISTICS:
(A) LENGTH: 23 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "CFTR EXON 21 PRIMER
SEQUENCE - SS#1"

(x i) SEQUENCE DESCRIPTION: SEQ ID NO:31:

CAAGTGAATC CTGAGCGTGA TTT    23

(2) INFORMATION FOR SEQ ID NO:32:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "CFTR EXON 21 PRIMER
SEQUENCE - SS#1"

(x i) SEQUENCE DESCRIPTION: SEQ ID NO:32:

CAAAAGTACC TGTTGCTCCA    20

(2) INFORMATION FOR SEQ ID NO:33:

(i) SEQUENCE CHARACTERISTICS:
(A) LENGTH: 25 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "CFTR EXON 21 PRIMER
SEQUENCE - SS#2"

(x i) SEQUENCE DESCRIPTION: SEQ ID NO:33:

GAACTTGATG GTAAGTACAT GGGTG    25

(2) INFORMATION FOR SEQ ID NO:34:

(i) SEQUENCE CHARACTERISTICS:
(A) LENGTH: 24 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "CFTR EXON 21 PRIMER
SEQUENCE - SS#2"

(x i) SEQUENCE DESCRIPTION: SEQ ID NO:34:

AGTCAAAAGT ACCTGTTGCT CCAG    24

(2) INFORMATION FOR SEQ ID NO:35:

(i) SEQUENCE CHARACTERISTICS:

(A) LENGTH: 20 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "CFTR EXON 21 PRIMER
SEQUENCE - SS#3"

(x i) SEQUENCE DESCRIPTION: SEQ ID NO:35:

TGATGGTAAG TACATGGGTG            20

(2) INFORMATION FOR SEQ ID NO:36:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "CFTR EXON 21 PRIMER
SEQUENCE - SS#3"

(x i) SEQUENCE DESCRIPTION: SEQ ID NO:36:

CAAAAGTACC TGTTGCTCCA            20

(2) INFORMATION FOR SEQ ID NO:37:

(i) SEQUENCE CHARACTERISTICS:
(A) LENGTH: 24 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "GCR 4-PLEX PRIMER SEQUENCE
- exon 6"

(x i) SEQUENCE DESCRIPTION: SEQ ID NO:37:

GGGTGGGAGG GTGGAGGCTA ATGG            24

(2) INFORMATION FOR SEQ ID NO:38:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "GCR 4-PLEX PRIMER SEQUENCE
- exon 6"

(x i) SEQUENCE DESCRIPTION: SEQ ID NO:38:

CCAGAAGGTA GAAAGGTGAG            20

(2) INFORMATION FOR SEQ ID NO:39:

(i) SEQUENCE CHARACTERISTICS:
(A) LENGTH: 19 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "GCR 4-PLEX PRIMER SEQUENCE
- exon 2"

(x i) SEQUENCE DESCRIPTION: SEQ ID NO:39:

GAATGTCCCA AGCCTTTGA            19

( 2 ) INFORMATION FOR SEQ ID NO:40:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "GCR 4-PLEX PRIMER SEQUENCE - exon 2"

( x i ) SEQUENCE DESCRIPTION: SEQ ID NO:40:

AAGCTGAAGC AAGAGAATCG        20

( 2 ) INFORMATION FOR SEQ ID NO:41:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "GCR 4-PLEX PRIMER SEQUENCE - exon 9"

( x i ) SEQUENCE DESCRIPTION: SEQ ID NO:41:

TGCAACTACT GAGGCACTT        19

( 2 ) INFORMATION FOR SEQ ID NO:42:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "GCR 4-PLEX PRIMER SEQUENCE - exon 9"

( x i ) SEQUENCE DESCRIPTION: SEQ ID NO:42:

TACAATGATG GGACTGTCG        19

( 2 ) INFORMATION FOR SEQ ID NO:43:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SCA 4-PLEX PRIMER SEQUENCE - exon 9"

( x i ) SEQUENCE DESCRIPTION: SEQ ID NO:43:

CATTTGCTTC TGACACAACT G        21

( 2 ) INFORMATION FOR SEQ ID NO:44:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SCA 4-PLEX PRIMER SEQUENCE

- exon 9"

( x i ) SEQUENCE DESCRIPTION: SEQ ID NO:44:

CCAACTTCAT CCACGTTCAC C                                                                 21

( 2 ) INFORMATION FOR SEQ ID NO:45:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "GCR 3-PLEX PRIMER SEQUENCE
            - exons 9, 10, 11"

( x i ) SEQUENCE DESCRIPTION: SEQ ID NO:45:

CCTTGCCCTG AACCCCGAA                                                                    19

( 2 ) INFORMATION FOR SEQ ID NO:46:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "GCR 3-PLEX PRIMER SEQUENCE
            - exons 9, 10, 11"

( x i ) SEQUENCE DESCRIPTION: SEQ ID NO:46:

CTGACTCTGT CCCTTTAATG CCCA                                                              24

( 2 ) INFORMATION FOR SEQ ID NO:47:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "TS 3- PLEX PRIMER SEQUENCE -
            exons 11, 12"

( x i ) SEQUENCE DESCRIPTION: SEQ ID NO:47:

GTGTGGCGAG AGGATATTCC A                                                                 21

( 2 ) INFORMATION FOR SEQ ID NO:48:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "TS 3- PLEX PRIMER SEQUENCE -
            exons 11, 12"

( x i ) SEQUENCE DESCRIPTION: SEQ ID NO:48:

TGGCTAGATG GGATTGGGTC T                                                                 21

( 2 ) INFORMATION FOR SEQ ID NO:49:

( i ) SEQUENCE CHARACTERISTICS:
        ( A ) LENGTH: 24 base pairs
        ( B ) TYPE: nucleic acid ( C ) STRANDEDNESS: single
( D ) TOPOLOGY: linear ( i i ) MOLECULE TYPE: other nucleic acid
( A ) DESCRIPTION: /desc = "TS 3- PLEX PRIMER SEQUENCE - exon 7"

( x i ) SEQUENCE DESCRIPTION: SEQ ID NO:49:

GGGTCCTACA ACCCTGTCAC CCAC 24

( 2 ) INFORMATION FOR SEQ ID NO:50:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "TS 3- PLEX PRIMER SEQUENCE - exon 7"

( x i ) SEQUENCE DESCRIPTION: SEQ ID NO:50:

AAGCTTCACT CTGAGCATAA CAAG 24

( 2 ) INFORMATION FOR SEQ ID NO:51:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "B- THALASSEMIA PRIMER SEQUENCE - exons 1, 2, 3"

( x i ) SEQUENCE DESCRIPTION: SEQ ID NO:51:

GCTGTCATCA CTTAGACCTC 20

( 2 ) INFORMATION FOR SEQ ID NO:52:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "B- THALASSEMIA PRIMER SEQUENCE - exons 1, 2, 3"

( x i ) SEQUENCE DESCRIPTION: SEQ ID NO:52:

GCAAGAAAGC GAGCTTAGTG 20

( 2 ) INFORMATION FOR SEQ ID NO:53:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "WT-1 PRIMER SEQUENCE - B"

( x i ) SEQUENCE DESCRIPTION: SEQ ID NO:53:

CTGAGTGAAT GGAGCGGC 18

( 2 ) INFORMATION FOR SEQ ID NO:54:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "WT-1 PRIMER SEQUENCE - B"

(xi) SEQUENCE DESCRIPTION: SEQ ID NO:54:

GGGTGAATGA GTAGGTGG      18

(2) INFORMATION FOR SEQ ID NO:55:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "WT-1 PRIMER SEQUENCE - F"

(xi) SEQUENCE DESCRIPTION: SEQ ID NO:55:

CGGTGCTGGA CTTTGCG      17

(2) INFORMATION FOR SEQ ID NO:56:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "WT-1 PRIMER SEQUENCE - F"

(xi) SEQUENCE DESCRIPTION: SEQ ID NO:56:

AAGTGGACAG TGAAGGCG      18

(2) INFORMATION FOR SEQ ID NO:57:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "WT-1 PRIMER SEQUENCE - H"

(xi) SEQUENCE DESCRIPTION: SEQ ID NO:57:

CCGTCTTGCG AGAGCACC      18

(2) INFORMATION FOR SEQ ID NO:58:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "WT-1 PRIMER SEQUENCE - H"

(xi) SEQUENCE DESCRIPTION: SEQ ID NO:58:

CTAATTTGCT GTGGGTTAGG      20

(2) INFORMATION FOR SEQ ID NO:59:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "WT-1 PRIMER SEQUENCE - J"

( x i ) SEQUENCE DESCRIPTION: SEQ ID NO:59:

AGTTGTGTAT ATTTGTGGTT ATG      23

( 2 ) INFORMATION FOR SEQ ID NO:60:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "WT-1 PRIMER SEQUENCE - J"

( x i ) SEQUENCE DESCRIPTION: SEQ ID NO:60:

GTTACTGTGG AAAGGCAATG      20

( 2 ) INFORMATION FOR SEQ ID NO:61:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "WT-1 PRIMER SEQUENCE - N"

( x i ) SEQUENCE DESCRIPTION: SEQ ID NO:61:

GAGATCCCCT TTTCCAG      17

( 2 ) INFORMATION FOR SEQ ID NO:62:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "WT-1 PRIMER SEQUENCE - N"

( x i ) SEQUENCE DESCRIPTION: SEQ ID NO:62:

CACAGCTGCC AGCAATG      17

( 2 ) INFORMATION FOR SEQ ID NO:63:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "WT-1 PRIMER SEQUENCE - 0"

( x i ) SEQUENCE DESCRIPTION: SEQ ID NO:63:

CTCACTGTGC CCACATTG      18

( 2 ) INFORMATION FOR SEQ ID NO:64:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "WT-1 PRIMER SEQUENCE - 0"

( x i ) SEQUENCE DESCRIPTION: SEQ ID NO:64:

CAATTTCATT CCACAATAG                                                                  1 9

( 2 ) INFORMATION FOR SEQ ID NO:65:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide primer"

( x i ) SEQUENCE DESCRIPTION: SEQ ID NO:65:

GCGGTCCCAA AAGGGTCAGT                                                                 2 0

UNIVERSAL PRIMER SEQUENCE FOR MULTIPLEX DNA AMPLIFICATION

FIELD OF THE INVENTION

This invention pertains to universal primers having use in amplification of DNA sequences by methods such as polymerase chain reaction (PCR), specifically to primers that allow the simultaneous amplification of a multiplicity of DNA sequences.

BACKGROUND OF THE INVENTION

Polymerase chain reaction (PCR) is a method whereby virtually any DNA sequence can be selectively amplified. The method involves using paired sets of oligonucleotides of predetermined sequence that hybridize to opposite strands of DNA and define the limits of the sequence to be amplified. The oligonucleotides prime multiple sequential rounds of DNA synthesis catalyzed by a thermostable DNA polymerase. Each round of synthesis is typically separated by a melting and re-annealing step, allowing a given DNA sequence to be amplified several hundred-fold in less than an hour (Saiki et al., *Science* 239:487, 1988).

The simplicity and reproducibility of these reactions has given PCR broad applicability. For example, PCR has gained widespread use for the diagnosis of inherited disorders and susceptibility to disease. Typically, the genomic region of interest is amplified from either genomic DNA or from a source of specific cDNA encoding the cognate gene product. Mutations or polymorphisms are then identified by subjecting the amplified DNA to analytical techniques such as DNA sequencing, hybridization with allele specific oligonucleotides, restriction endonuclease cleavage or single-strand conformational polymorphism (SSCP) analysis.

For the analysis of small genes or genes where the mutant allele or polymorphism is well characterized, amplification of single defined regions of DNA is sometimes sufficient. When analyzing large and/or undefined genes, however, multiple individual PCR reactions are often required to identify critical base changes or deletions. Thus, to streamline the analysis of large complex genes, multiplex PCR (i.e., the simultaneous amplification of different target DNA sequences in a single PCR reaction) has been utilized.

The results obtained with multiplex PCR are, however, frequently complicated by artifacts of the amplification procedure. These include "false-negative" results due to reaction failure and "false-positive" results such as the amplification of spurious products, which may be caused by annealing of the primers to sequences which are related to, but distinct from, the true recognition sequences.

For use in multiplex PCR, a primer should be designed so that its predicted hybridization kinetics are similar to those of the other primers used in the same multiplex reaction. While the annealing temperatures and primer concentrations may be calculated to some degree, conditions generally have to be empirically determined for each multiplex reaction. Since the possibility of non-specific priming increases with each additional primer pair, conditions must be modified as necessary as individual primer sets are added. Moreover, artifacts that result from competition for resources (e.g., depletion of primers) are augmented in multiplex PCR, since differences in the yields of unequally amplified fragments are enhanced with each cycle. Given these limitations, the development of a new diagnostic test can be very labor-intensive and costly.

Weighardt et al. (*PCR Methods and App.* 3:77, 1993) describe the use of 5'-tailed oligonucleotides for PCR. However, a key feature of this amplification method involves separate annealing and primer extension reactions for each primer, which is not practical in a multiplex context.

Thus, there is a need in the art for primers that allow multiplex PCR reactions to be designed and carried out without elaborate optimization steps, irrespective of the potentially divergent properties of the different primers used. Furthermore, there is a need in the art for primers that allow multiplex PCR reactions that simultaneously produce equivalent amounts of each one of many amplification products.

SUMMARY OF THE INVENTION

This invention pertains to primers that allow simultaneous amplification of multiple DNA target sequences present in a DNA sample. According to the invention, the DNA sample in a single reaction mixture is contacted with a multiplicity of paired oligonucleotide primers having the structure 5'-XY-3', wherein: X comprises a sequence that does not hybridize to the target sequence; the melting temperature of a hybrid between X and its complement in the absence of other sequences is greater than about 60° C.; and Y comprises a sequence contained within or flanking the target sequence or its complement.

Multiple cycles of melting, reannealing, and DNA synthesis (i.e., a PCR reaction) are thereafter performed with the above mentioned DNA sample and the oligonucleotide primers. Preferably, X comprises the sequence 5'-GCGGTCCCAAAAGGGTCAGT-3' SEQ ID NO: 65. Amplified target sequences may then be detected by any method, including, for example, hybridization with allele-specific oligonucleotides, restriction endonuclease cleavage, or single-strand conformational polymorphism (SSCP) analysis.

The invention also encompasses a method for detecting multiple defined target DNA sequences in a DNA sample. This method is carried out by performing the same procedure set forth above, in which the 3' sequence of one primer of each pair comprises a target DNA sequence itself or its complement. The method includes a further step of detecting the amplification products, preferably by gel electrophoresis. In this embodiment, the presence or absence of an amplification product is diagnostic of the presence or absence of the target sequence in the original DNA sample.

In another aspect, the invention encompasses methods for high-throughput genetic screening. The method, which allows the rapid and simultaneous detection of multiple defined target DNA sequences in DNA samples obtained from a multiplicity of individuals, is carried out by simultaneously amplifying many different target sequences from a large number of patient DNA samples, using oligonucleotide primer pairs as above.

In yet another aspect, the present invention provides single-stranded oligonucleotide DNA primers for amplification of a target DNA sequence in a multiplex polymerase chain reaction. The primers have the structure 5'-XY-3', wherein X comprises the sequence 5'-GCGGTCCCAAAAGGGTCAGT-3' (SEQ ID NO: 65), and Y comprises a sequence contained within or flanking a target sequence or its complement. Typically, Y comprises a sequence from 17 to 25 bases in length, and the melting temperature of hybrids between the primers and their complements is at least 72° C. or 0.5M NaCl.

The methods and compositions of the present invention can be applied to the diagnosis of genetic and infectious diseases, gender determination, genetic linkage analysis, and forensic studies.

BRIEF DESCRIPTION OF THE DRAWINGS

FIGS. 1A and 1B are a table listing amplicon-specific oligonucleotide primer sequences (SEQ ID NO: 1 through SEQ ID NO: 64).

DETAILED DESCRIPTION OF THE INVENTION

Figures 2A, 2B:
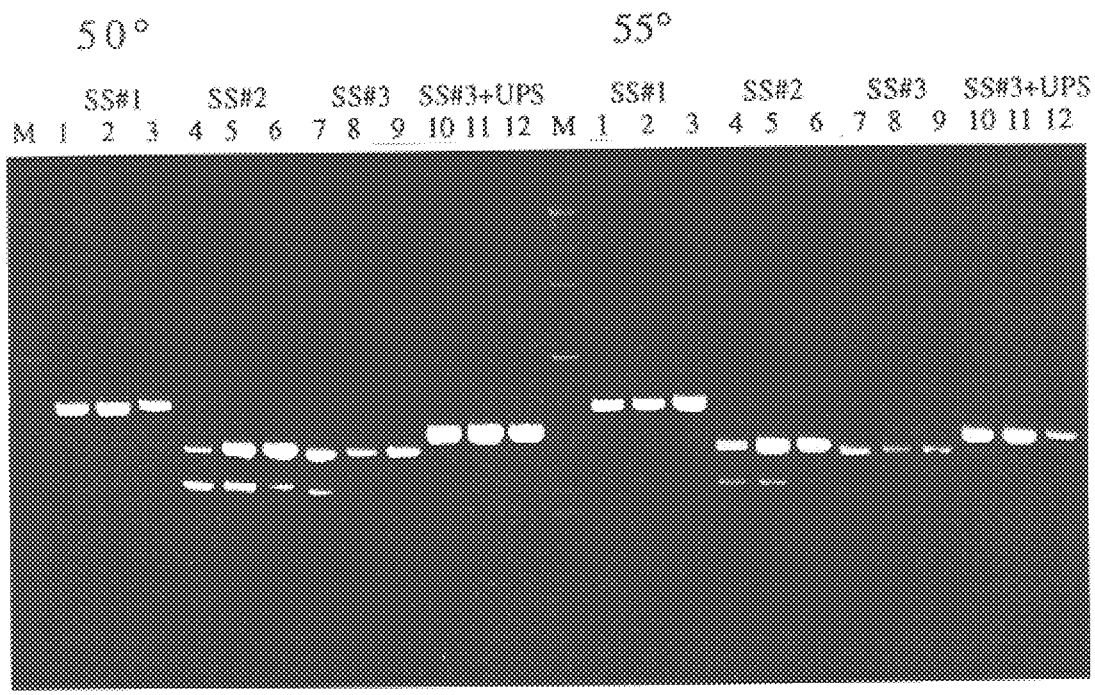
FIGS. 2A–2D are an illustration of an agarose gel in which PCR amplification products corresponding to exon 21 of the CFTR gene are resolved.
Figures 2C, 2D:
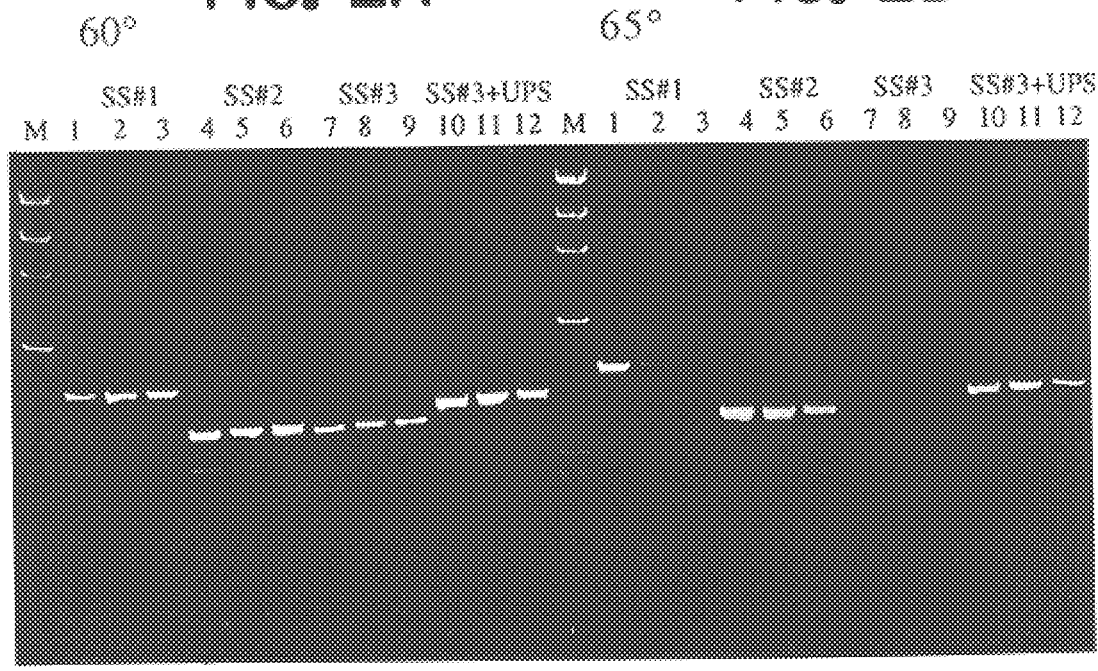

All patent applications, patents, and literature references cited in this specification are hereby incorporated by reference in their entirety. In case of conflict, the present description, including definitions, will control.

Definitions:

1. "Amplification" of DNA as used herein denotes the use of polymerase chain reaction (PCR) to increase the concentration of a particular DNA sequence within a mixture of DNA sequences. An "amplicon" is a target DNA sequence that is amplified by PCR.

2. "Multiplex PCR" as used herein refers to the simultaneous amplification of multiple DNA targets in a single polymerase chain reaction (PCR) mixture.

3. "High-throughput" denotes the ability to simultaneously process and screen a large number of DNA samples (e.g. in excess of 100 genomic DNAs) in a rapid and economical manner, as well as to simultaneously screen large numbers of different genetic loci within a single DNA sample.

The present invention encompasses methods and compositions that allow the efficient and essentially simultaneous amplification of different target DNA sequences in a single polymerase chain reaction (i.e., multiplex PCR). Preferably, equivalent amounts of each amplification product are obtained. The method utilizes novel chimeric oligonucleotide primers that circumvent the technical difficulties associated with multiplex PCR that result in unequal amplification of different target sequences in the same reaction mix.

For example, in a standard PCR reaction employing more than a single pair of oligonucleotide primers, the obligatory imposition of a single set of reaction conditions generally means that one of the primer sets will function more efficiently in priming, causing the target sequence specified by that set of primers to be selectively amplified in the early cycles of amplification. Furthermore, the more efficient primers will also be depleted from the reaction sooner than the less efficient ones, resulting in the increased accumulation of non-specific amplification products in later cycles of amplification. Clearly, these problems are magnified when it is desired to use multiple primer pairs (>3–4) in a single reaction.

The methods and compositions of the present invention circumvent these problems by imposing a uniformly high degree of specificity on the annealing reactions that occur between different primers present in the mixture and their cognate target sequences in the DNA template. During the early cycles of amplification, products are synthesized that contain the chimeric primers on either end. The chimeric primers then serve as high stringency recognition sequences for subsequent rounds of amplification. This results in normalizing the annealing efficiency of different primers and their cognate target sequences, and thus also normalizes the degree of amplification of different targets.

Primer Design

Multiplex PCR according to present invention utilizes chimeric oligonucleotide primers that include two domains. The 5' "half" of each primer may comprise any sequence between 17 and 25 bases in length that is unrelated to the target DNA, and has the property of forming hybrids with relatively high melting temperatures (e.g., $T_m$s>60° C. in the absence of other sequences). In some applications, when the target DNA sequence is embedded in a sequence of low complexity (i.e., <$10^8$ bp), primers may be used that form hybrids with lower melting temperatures. In a preferred embodiment, the 5' sequence comprises 5'-GCGGTCCCAAAAGGGTCAGT-3' (SEQ ID NO: 65). This sequence, which is designated as a "universal primer sequence" (UPS), is derived from the bacteriophage vector M13mp18 (Messing J., *Meth. Enzymol.* 101:20, 1983).

The 3' "half" of each primer comprises a target-specific sequence, i.e., a sequence that is either present or potentially present in the target DNA or its complement. These 3' sequences may comprise without limitation any such sequence of 17–25 bases, and preferably 20 bases, irrespective of the melting temperatures of hybrids formed between the isolated sequence and its complement.

In one embodiment, the 3' half of the primer is intended to hybridize with a genomic sequence flanking the target sequence of interest; in this case, the primer is used to amplify the target sequence for subsequent diagnostic tests such as, e.g., hybridization with allele-specific oligonucleotides, restriction endonuclease cleavage, or single-strand conformational polymorphism (SSCP) analysis. For this purpose, the 3' half of the primer must correspond to a sequence known to be present in all DNA samples to be tested (or its complement). Non-limiting examples of 3' primer halves useful in practicing the present invention are shown in FIGS. 1A and 1B.

In another embodiment, the amplification reaction itself serves as the critical diagnostic step. In this case, the 3' sequence of the primer corresponds to a defined wild-type version of a particular amplicon or its complement (or to a variant version or its complement) whose presence or absence is being tested. When such allele-specific sequences are incorporated into chimeric PCR primers according to the present invention, and the chimeric primers are used in amplification reactions, the absence of a given amplification product is considered definitive for the absence of the allele in the DNA sample being tested.

For use in a given multiplex PCR reaction, target-specific primer sequences are typically analyzed as a group to evaluate the potential for fortuitous dimer formation between different primers. This evaluation may be achieved using commercially available computer programs for sequence analysis, such as *Gene Runner*, Hastings Software Inc. Other variables, such as the preferred concentrations of $Mg^{+2}$, dNTPs, polymerase, and primers, are optimized using methods well-known in the art (Edwards et al., *PCR Methods and Applications* 3:565,1994).

DNA templates

Any DNA sample may be used in practicing the present invention, including without limitation eukaryotic, prokaryotic and viral DNA. In a preferred embodiment, the target DNA represents a sample of genomic DNA isolated from a patient. This DNA may be obtained from any cell source or body fluid. Non-limiting examples of cell sources available in clinical practice include blood cells, buccal cells, cervicovaginal cells, epithelial cells from urine, fetal cells, or any cells present in tissue obtained by biopsy. Body fluids include blood, urine, cerebrospinal fluid, semen and tissue exudates at the site of infection or inflammation. DNA is extracted from the cell source or body fluid using any of the numerous methods that are standard in the art. It will be understood that the particular method used to extract DNA will depend on the nature of the source. The preferred amount of DNA to be extracted for use in the present invention is at least 5 pg (corresponding to about 1 cell equivalent of a genome size of $4 \times 10^9$ base pairs).

Multiplex PCR reaction conditions

In practicing the present invention, a DNA sample is contacted with pairs of chimeric oligonucleotide primers under conditions suitable for polymerase chain reaction. Standard PCR reaction conditions may be used, e.g., 1.5 mM $MgCl_2$, 50 mM KCl, 10 mM Tris-HCl, pH 8.3, 200 µM deoxynucleotide triphosphates (dNTPs), and 25–100 U/ml Taq polymerase (Perkin-Elmer, Norwalk, Conn.).

The concentration of each chimeric primer in the reaction mixture can range from about 0.05 to about 4 µM. The optimal concentration for primer is evaluated by performing single PCR reactions using each primer pair individually. Similarly, each primer pair is evaluated independently to confirm that all primer pairs to be included in a single multiplex PCR reaction require the same amplification conditions (i.e., temperature, duration of annealing and extension steps). It was found (see example below) that all chimeric primers containing the M13 derived UPS as the 5' half of their sequence could be used at a broad range of annealing temperatures (i.e., 50°–60° C.).

Multiplex PCR reactions are carried out using manual or automatic thermal cycling. Any commercially available thermal cycler may be used, such as, e.g., Perkin-Elmer 9600 cycler.

Finally, the reaction products are analyzed using any of several methods that are well-known in the art. Preferably, agarose gel electrophoresis is used to rapidly resolve and identify each of the amplified sequences. In a multiplex reaction, different amplified sequences are preferably of distinct sizes and thus can be resolved in a single gel. In one embodiment, the reaction mixture is treated with one or more restriction endonucleases prior to electrophoresis. Alternative methods of product analysis include without limitation dot-blot hybridization with allele-specific oligonucleotides and SSCP.

The following examples are intended to further illustrate the present invention without limiting the invention thereof.

EXAMPLE 1: Effect of Chimeric Primers on Efficiency and Specificity of Amplification The following experiment was done to evaluate the effects on amplification of incorporating the M13 UPS sequence into PCR primers.

A. METHODS

Primer design:

Three sequence-specific primer pairs used to amplify Exon 21 of the cystic fibrosis transmembrane regulator (CFTR) gene (Kerem et al., *Science* 245:1073, 1989) are shown in FIGS. 1A and 1B. A chimeric version of one of the three primers was synthesized containing the M13 UPS sequence 5'-GCGGTCCCAAAAGGGTCAGT-3' (SEQ ID NO: 65) immediately 5' to the illustrated sequences. The oligonucleotides were synthesized using conventional chemistry and were purified by high-performance liquid chromatography prior to use.

DNA preparation:

Whole blood samples were collected in high glucose ACD Vacutainers™ (Beckton Dickenson & Co., Franklin Lanes, N.J.). Following centrifugation, the buffy coat was collected and lysed with two washes of a 10:1 (v/v) solution of 14 mM $NH_2Cl$ and 1 mM $NaHCO_3$. The nuclei were harvested by centrifugation, resuspended in lysis buffer (10 mM Tris-HCl, pH 8.0, 0.4M NaCl, 2 mM EDTA, 0.5% SDS, 500 µg/ml proteinase K) and incubated overnight at 37° C. Samples were then extracted with ¼th volume of saturated NaCl, and the DNA was collected by ethanol precipitation. The final DNA pellet was washed with 70% ethanol, air dried and dissolved in TE (10 mM Tris-HCl, pH 7.5, 1 mM EDTA).

Amplification reactions:

For single amplifications, 50 µl reaction mixtures were prepared containing 2 µg of genomic DNA prepared as described above in 1X PCR buffer (10 mM Tris-HCl, pH 8.3, 50 mM KCl, 1.5 mM MgCl), 200 µM dNTPs, and 2.5 units Taq polymerase (Perkin-Elmer, Norwalk, Conn.). Multiplex PCR reactions were carried in a volume of 100 µl under the same conditions, except that 10 units of Taq polymerase per reaction was used. Primer concentrations ranged from 0.25 to 1.0 µM. Amplifications were carried out using a Perkin-Elmer 9600 themocycler (Perkin-Elmer, Norwalk, Conn.) for 28 cycles with ramping (melting at 94° C. for 10 s, annealing at 50° C., 55° C., 60° C., or 65° C. for 10 s, and extension at 72° C. for 10 s).

After completion of the reaction, 8 µl of the reaction products were loaded directly onto a 2% ethidium bromide-stained agarose gel and subjected to electrophoresis at 250 volts for 90 minutes. The amplification products were visualized with a UV transilluminator and photographed with an Alpha Innotech IS-500 Digital Imaging System version 1.97 (Sun BIO Science, Inc., Branford, Conn.).

B. RESULTS

The efficiencies with which the three CFTR primer pairs (designated SS#1, SS#2, and SS#3) primed amplification varied with primer concentration and temperature of annealing (FIGS. 2A–2D). The primer concentrations were as follows: Lanes 1, 4, 7, and 10, 1.0 μM; lanes 2, 5, 8, and 11, 0.5 μM; and lanes 3, 6, 9, and 12, 0.25 μM. The temperatures of annealing were 50° C., 55° C., 60° C. and 65° C., as indicated.

The SS#1 and SS#3 primers, for example, were noticeably inefficient at annealing temperatures above 60° C. The primer pair designated SS#3-UPS, which corresponds to the SS#3 primers having the M13 UPS sequence on their 5' termini, was highly efficient in priming at all temperatures tested; furthermore, few spurious amplification products were detected in reactions containing SS#3-UPS primers. By contrast, SS#2 primers gave spurious amplification products at all three temperatures below 65° C.

EXAMPLE 2: Comparison of Multiplex PCR Reactions Using CFIR Primer Pairs Lacking and Containing M13 UPS Fifteen primer pairs that were used to amplify sequences contained in different exons of the CFTR gene are shown in FIGS. 1A and 1B. A parallel set of primers was synthesized in which the M13 UPS sequence was present 5' to the CFTR-specific sequences.

DNA prepared as described in Example 1 was incubated simultaneously with all fifteen UPS-containing or -lacking primer pairs, and amplification reactions were carried out using identical conditions (e.g., 60° C. annealing temperature). Identical reaction conditions, cycling times and primer concentrations were used for both primer sets.

Figure 3:
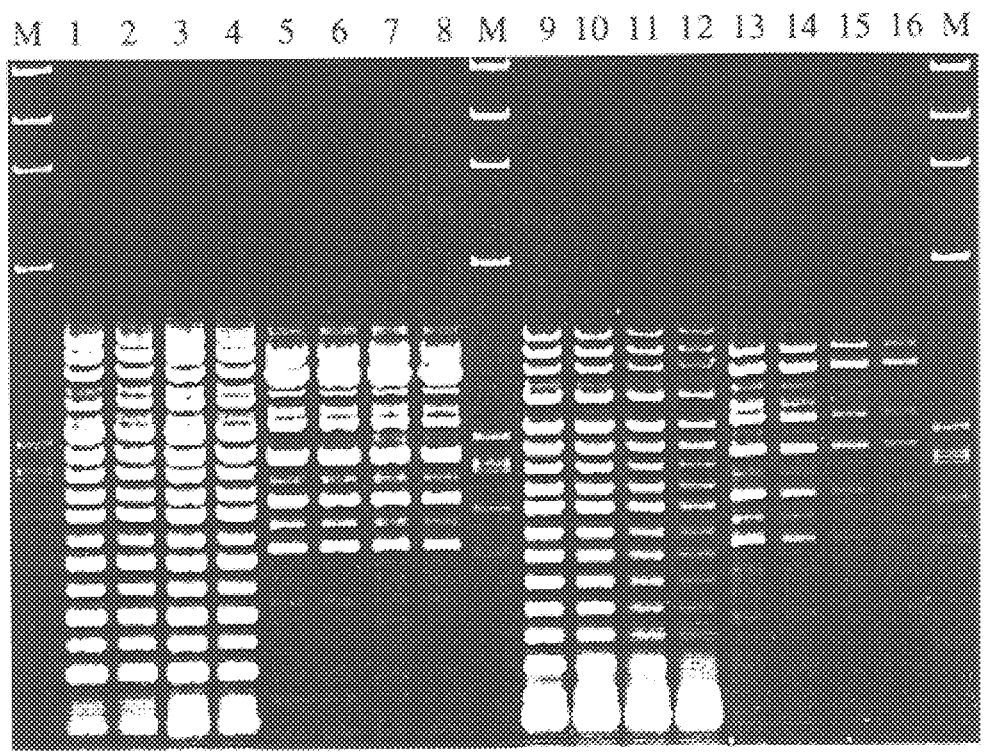
FIG. 3 is an illustration of an agarose gel in which PCR amplification products corresponding to exons 3, 4, 5, 7, 9, 10, 11, 12, 13, 14b, 17b, 19, 20, 21, and intron 19 of the CFTR gene are resolved. Lanes 1–8 represent products derived from genomic DNA samples isolated from blood cells, while in lanes 9–12 the genomic DNA template was derived from buccal cells. Lanes 1–4 and 9–12 show the amplification products obtained using chimeric primers according to the present invention; lanes 5–8 and 13–16 show amplification products obtained using sequence-specific primers. Lane M shows the electrophoretic pattern of φX174 Hae III-digested marker DNA. The correspondence between exon designation and size is shown FIGS. 1A and 1B.

As shown in FIG. 3, PCR reactions using the standard sequence-specific primer pairs fail to generate a clear multiplex PCR profile of the CFTR locus. Specifically, several of the expected bands are clearly under-represented due to differential amplification (FIG. 3, lanes 5–8 and lanes 13–16). In contrast, a clear multiplex profile is obtained when the CFTR locus is amplified with the corresponding UPS tagged primer pairs. The expected bands are clearly prominent and the profiles are virtually free of contaminating non-specific products (FIG. 3, lanes 1–4 and 9–12). Moreover, equivalent banding patterns are observed over an 8-fold range of template concentrations when the UPS tagged primer pairs are employed. Conversely, the amplification profile generated using the non-tagged standard primer sets is sensitive to variations in the template concentration as evidenced by the changes in the intensity of individual bands (FIG. 3, lanes 5–8 and 13–16).

EXAMPLE 3: Use of Multiplex PCR to Simultaneously Amplify Different Disease-related Sequences Under Identical Conditions DNA was isolated as described in Example 1 above and subjected to multiplex PCR amplification using different combinations of UPS-tagged and untagged primers (FIGS. 1A and 1B).

Figure 4:
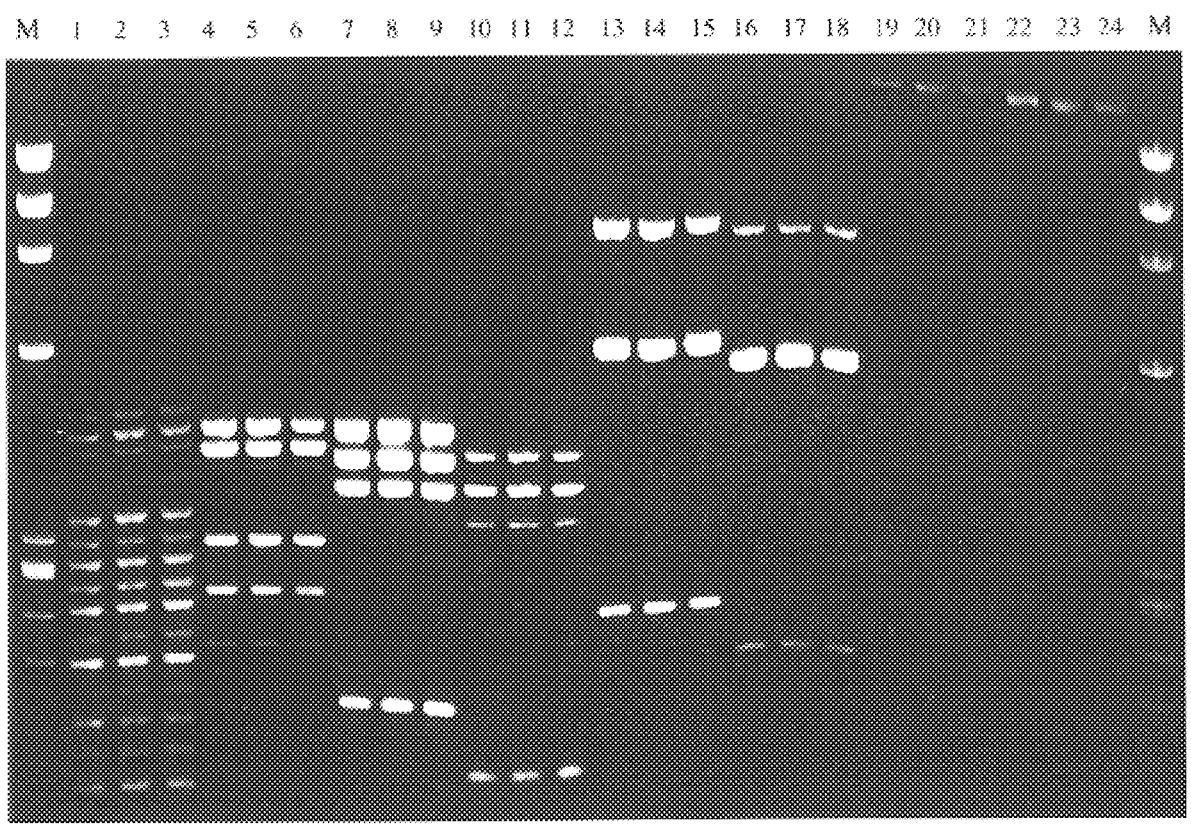
FIG. 4 is an illustration of an agarose gel in which the products of a single PCR amplification assay for multiple gene loci are resolved. The loci correspond to the CFTR locus as in FIG. 3 (lanes 1–6); α-galactosidase and sickle-cell genes (lanes 7–12); α-galactosidase and Tay-Sachs genes (lanes 13–18), and β-thalassemia (lanes 19–24). In lanes 1–3, 5–8, 13–15 and 19–21, chimeric primers according to the present invention were used for amplification. In lanes 4–6, 9–12, 16–18 and 22–24, the corresponding sequence-specific non-chimeric primers were used.

The banding patterns for the following primer sets are displayed in FIG. 4: lanes 1–3 and 4–6, CFTR locus; lanes 7–9 and 10–12, α-galactosidase (Gaucher's disease, GCR, Kornreich et al., *Nucleic Acids Res.* 17:3301, 1989) and Sickle Cell Anemia, (SCA, Navon et al., *Science* 243:1471, 1989); lanes 13–15 and 16–18, GCR and Tay-Sachs (TS, Tanaka et al., *Am. J. Hum. Genet.* 46:329, 1990); lanes 19–21 and 22–24, β-thalassemia. Amplification of the human WT1 gene (Wilms tumor, Varanasi et al., *Proc.Nat.l.Acad.Sci.* USA 91:3554, 1994) using 6 primer pairs is presented in FIG. 5. For the multiplex PCR reactions displayed in FIG. 4, the UPS tagged primer pairs generate only the desired bands. FIG. 4 further demonstrates that the UPS tagged primers yield co-amplified products that are more uniform with respect to the band intensities than the corresponding products generated from the non-tagged sequence specific primers (lanes 1–6, 7–12 and 13–18).

Figure 5:
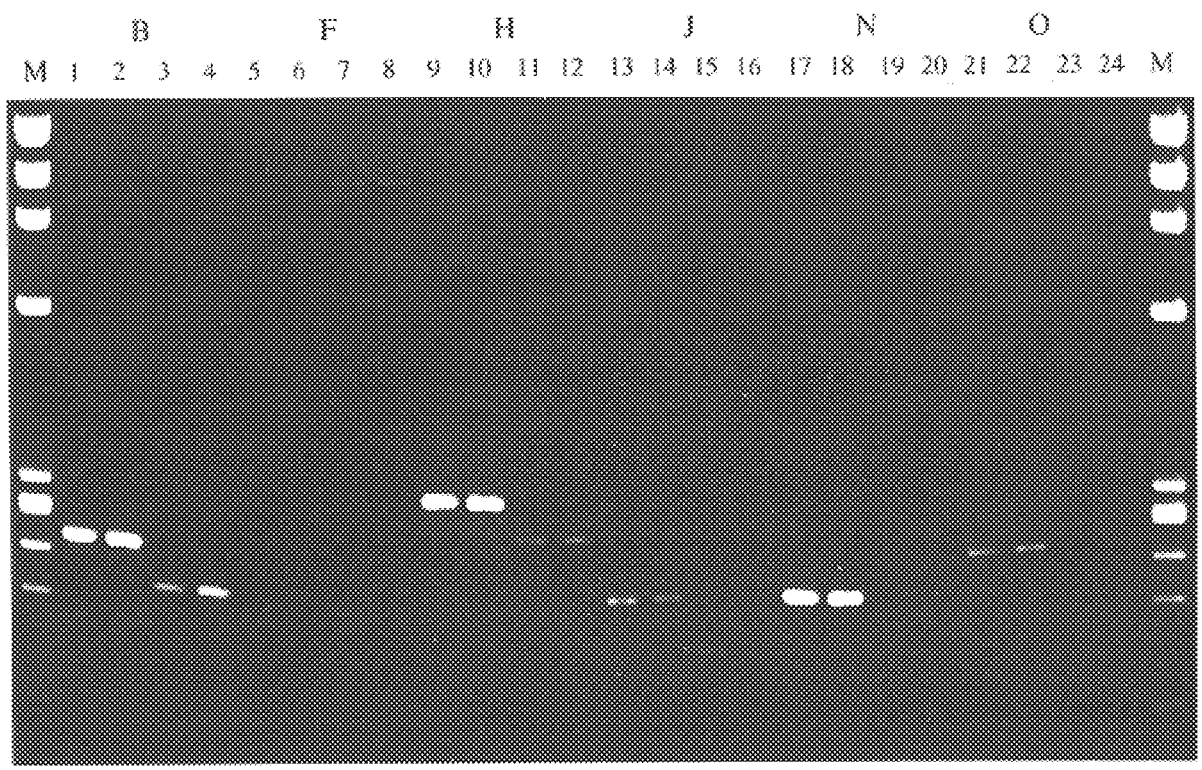
FIG. 5 is an illustration of an agarose gel in which PCR amplification products are resolved corresponding to different segments of the human WT-1 gene. The products shown in lanes 1, 2, 5, 6, 9, 10, 13, 14, 17, 18, 21, 22 were amplified with chimeric primer pairs designed according to the present invention. The products shown in lanes 3, 4, 7, 8, 11, 12, 15, 16, 19, 20, 23, 24 were amplified with the corresponding sequence-specific primers. Amplifications represent each of six amplicons within the WT-1 gene (B, F, H, J, N, and O; see Table 1). Lane M is φX174 Hae III-digested marker DNA.

For 13 of the 14 UPS-tagged primer pairs, the expected bands are clearly prominent and virtually free of spurious amplification products. With the exception of one primer pair (FIG. 5, lanes 5 and 6), which does not generate a detectable product when the chimeric primer is employed, the presence of the UPS sequence enhances the yield of the respective PCR products (FIG. 5, lanes 1–4, 9–12, 17–20 and 21–24).

I claim:

1. A multiplicity of single-stranded oligonucleotide DNA primers for simultaneous amplification of multiple target DNA sequences under a single set of reaction conditions in a single multiplex polymerase chain reaction (PCR), said primers having a 5' X domain and a 3' Y domain, wherein;
   a) each said 5' X domain comprises a common sequence that does not hybridize to and has no homology with any one of said multiple target DNA sequences or its complement, whereby the synthesis of spurious amplification products are prevented;
   b) the melting temperature of a hybrid between X and its complement in the absence of other sequences is greater than about 60° C.;
   c) each said 3'Y domain comprises a unique sequence contained within or flanking one of said multiple target DNA sequences or its complement whereby the synthesis of spurious amplification products are prevented; and
   d) the melting temperature of a hybrid between at least one of said 3'-Y domains and its complement, in the absence of other sequences, is different from the melting temperature of a hybrid between at least one other 3'-Y domain and its complement present in said multiplex PCR; and
   e) each of said primers being capable of annealing specifically with it cognate target sequence under uniform high stringency annealing conditions during said amplification.

2. The multiplicity of single-stranded oligonucleotide DNA primers according to claim 1, wherein X comprises the sequence 5'-GCGGTCCCAAAAGGGTCAGT-3' (SEQ ID NO: 65).

3. The multiplicity of single-stranded oligonucleotide DNA primers according to claim 1, wherein X and Y each comprise from 17 to 20 bases.

4. The multiplicity of single-stranded oligonucleotide DNA primers according to claim 1, wherein the melting temperature of a hybrid formed between each of said primers and its complement in a solution of 0.5M NaCl is at least 72° C.

5. A multiplicity of single-stranded oligonucleotide DNA primers for simultaneous amplification of multiple target DNA sequences under a single set of reaction conditions in a single multiplex polymerase chain reaction (PCR), wherein said primers consist of the sequence 5'-GCGGTCCCAAAAGGTCAGT (SEQ ID NO: 65) (Y)-3', wherein an individual Y comprises a unique sequence contained within or flanking one of said multiple target DNA sequences or its complement.

6. A method for simultaneous amplification of multiple target DNA sequences present in a DNA sample, said method comprising:
   a) contacting said DNA sample, in a single reaction mixture, with a multiplicity of single-stranded oligonucleotide DNA primer pairs having a 5' X domain, and a 3'Y domain, wherein
      (i) each said X domain comprises the common sequence 5'-GCGGTCCCAAAAGGGTCAGT-3' (SEQ ID NO: 65), whereby the synthesis of spurious amplification products are prevented, and
      (ii) each said Y domain comprises a unique sequence contained within or flanking one of said multiple target sequences or its complement, whereby the synthesis of spurious amplification products are prevented; and
   b) performing multiple cycles of melting, reannealling, and DNA synthesis under identical reaction conditions and cycling parameters.

7. A method for simultaneously detecting the presence of multiple target DNA sequences in a DNA sample, which comprises the steps of:
   a) simultaneously contacting said DNA sample, in a single reaction mixture, with a multiplicity of single-stranded oligonucleotide DNA primer pairs, each of said multiplicity of single-stranded oligonucleotide DNA primer pairs consisting of a first oligonucleotide DNA primer and a second oligonucleotide DNA primer, wherein
      (i) said first oligonucleotide DNA primer has a 5' X domain and a 3'Y domain, wherein each said X domain comprises the common sequence 5'-GCGGTCCCAAAAGGGTCAGT-3' (SEQ ID NO: 65) and each said Y domain comprises a unique sequence contained within or flanking one of said multiple target DNA sequences or its complement, and (ii) said second oligonucleotide DNA primer has a 5' X domain and a 3'Y domain, wherein each said X domain comprises the common sequence 5'-GCGGTCCCAAAAGGGTCAGT-3' (SEQ ID NO: 65), and each said Y domain comprises a unique sequence contained within or flanking one of said multiple target DNA sequences or its complement, whereby the synthesis of spurious amplification products are prevented; and b) performing multiple cycles of melting, reannealing, and DNA synthesis under identical reaction conditions and cycling parameters to form amplification products for each of said multiple target DNA sequences amplified with said multiplicity of single-stranded oligonucleotide DNA primers; and c) detecting said amplification products.

8. The method according to claim 7, wherein detection of said amplification products indicates the presence of said multiple target DNA sequences in said DNA sample.

9. The method according to claim 7, wherein said step of detecting comprises gel electrophoresis.

10. A method for high-throughput genetic screening to simultaneously detect the presence of multiple target DNA sequences in DNA sample(s) obtained from one or more individuals, said method comprising the steps of:

a) simultaneously contacting said DNA sample(s) with a multiplicity of single-stranded oligonucleotide DNA primer pairs, each of said pairs consisting of a first oligonucleotide DNA primer and a second oligonucleotide DNA primer, wherein (i) said first oligonucleotide DNA primer of each pair has a 5' X domain and a 3'Y domain, wherein each X domain comprises the common sequence 5'-GCGGTCCCAAAAGGGTCAGT-3' (SEQ ID NO: 65) and each Y domain comprises a unique sequence contained within or flanking one of said multiple target DNA sequences or its complement, and (ii) said second primer of each pair has a 5' X domain and a 3'Y domain, wherein each X domain comprises the common sequence 5'-GCGGTCCCAAAAGGGTCAGT-3' (SEQ ID NO: 65), and each Y domain comprises a unique sequence contained within or flanking one of said multiple target sequences or its complement, whereby the synthesis of spurious amplification products are prevented, b) subjecting said sample to multiple cycles of melting, reannealing, and DNA synthesis wherein each of said cycles is conducted under the same reaction conditions and cycling parameters to form amplification products for each of said multiple target DNA sequences; and c) detecting said amplification products.

11. The method according to claim 10, wherein detection of said amplification products indicates the presence of said multiple target DNA sequence(s) in said DNA sample(s).

12. The method according to claim 10, wherein said step of detecting comprises gel electrophoresis.

13. A method for simultaneously detecting amplification products of multiple target DNA sequence(s) in a DNA sample(s), said method comprising the steps of:

a) simultaneously contacting said DNA sample(s) with a multiplicity of single-stranded oligonucleotide DNA primer pairs, each of said pairs consisting of a first oligonucleotide DNA primer and a second oligonucleotide DNA primer each having a 5' X domain and a 3'Y domain, wherein (i) said X domain in said first oligonucleotide DNA primer comprises the common sequence 5'-GCGGTCCCAAAAGGGTCAGT-3' (SEQ ID NO: 65) and said Y domain comprises a unique sequence contained within or flanking one of said multiple target DNA sequence or its complement, and (ii) said X domain in said second oligonucleotide DNA primer comprises the common sequence 5'-GCGGTCCCAAAAGGGTCAGT-3' (SEQ ID NO: 65), and said Y domain comprises a unique sequence contained within or flanking one or said multiple target DNA sequences or its complement;

c) subjecting said sample(s) to multiple cycles of melting, reannealing, and DNA synthesis wherein each of said cycles is conducted under the same conditions and cycling parameters to form amplification products for each of said multiple target DNA sequences primed with said oligonucleotides, and d) detecting said amplification products.

14. A method of screening to simultaneously detect amplification products of multiple target DNA sequences in DNA sample(s), said method comprising the steps of:

a) contacting said DNA sample(s) with a multiplicity of single-stranded oligonucleotide DNA primer pairs having a 5'X domain, and a 3'Y domain, under signal multiplex polymerase chain reaction conditions wherein coamplification of said multiple target DNA sequences occurs in one or more cycles of identical melting, annealing and extending temperatures and times, wherein each said X domain comprises a common sequence that is neither complementary to nor specific for said multiple target DNA sequences, whereby the synthesis of spurious amplification products are prevented; and each said Y domain comprises a unique sequence, wherein said unique sequence is complementary to and specific for one of said multiple target DNA sequences suspected to be present in said DNA sample(s), whereby the synthesis of spurious amplification products are prevented; and b) detecting said amplification products.

15. The method according to claim 14, wherein said multiple target DNA sequences are located within different regions of a gene present in said DNA sample(s).

16. The method according to claim 14, wherein said multiple target DNA sequences are located within multiple genes present in said DNA sample(s).

17. A multiplicity of amplified target DNA sequences free of spurious amplification products produced according to the method of a) simultaneously contacting a DNA sample(s) with a multiplicity of single-stranded oligonucleotide DNA primer pairs, each of said pairs consisting of a first oligonucleotide DNA primer and a second oligonucleotide DNA primer each having a 5'X domain and a 3'Y domain, wherein (i) said X domain in said first oligonucleotide DNA primer comprises the common sequence 5'-GCGGTCCCAAAAGGGTCAGT-3' (SEQ ID NO: 65) and said Y domain comprises a unique sequence contained within or flanking one of said multiple target DNA sequences or its complement, and (ii) said X domain in said second oligonucleotide DNA primer comprises the common sequence 5'-GCGGTCCCAAAAGGGTCAGT-3' (SEQ ID NO: 65), and said Y domain comprises a unique sequence contained within or flanking one of said multiple target DNA sequences or its complement;

c) subjecting said sample(s) to multiple cycles of melting, reannealing, and DNA synthesis wherein each of said cycles is conducted under the same conditions and cycling parameters, whereby a multiplicity of amplified target DNA sequences are obtained.

18. A multiplicity of amplified target DNA sequences free of spurious amplification products produced according to the method of contacting a DNA sample(s) with a multiplicity of single-stranded oligonucleotide DNA primer pairs having a 5'X domain, and a 3'Y domain, under single multiplex polymerase chain reaction conditions wherein coamplification of multiple target DNA sequences occurs in one or more cycles of identical melting, annealing and extending temperatures and times, wherein each said X domain comprises a common sequence that is neither complementary to nor specific for said multiple target DNA sequences, whereby the synthesis of spurious amplification products are prevented; and each said Y domain comprises a unique sequence, wherein said unique sequence is complementary to and specific for one of said multiple target DNA sequences suspected to be present in said DNA sample, whereby the synthesis of spurious amplification products are prevented; and, whereby a multiplicity of amplified target DNA sequences are obtained.

\* \* \* \* \*

UNITED STATES PATENT AND TRADEMARK OFFICE
CERTIFICATE OF CORRECTION

PATENT NO. : 5,882,856
DATED : March 16, 1999
INVENTOR(S) : Anthony P. Shuber

It is certified that error appears in the above-identified patent and that said Letters Patent is hereby corrected as shown below:

Title page,
Item [56], "Bio/Technology" should read -- *Bio/Technology* --;
Item [56], "specificty" should read -- specificity --;
Item [56], "11418" should read -- 1418 --;
Item [56], "*Bio Techniques*" should read -- *BioTechniques* --;
Item [56], "Populatin" should read -- Population --;
Item [56], "*Genet...*" should read -- *Genet.,* --;
Item [56], "Termodynamic" should read -- Thermodynamic --.

Column 2,
Line 29, "SEQ ID NO: 65" should read -- (SEQ ID NO: 65) --;
Line 63, "or" should read -- in --.

Column 4,
Line 64, "known" should read -- *known* --.

Column 5,
Line 60, "50°-60° C." should read -- 50-60°C --.

Column 6,
Line 54, "C." should read -- C --;
Line 34, "NH$_2$Cl" should read -- NH$_4$Cl --;
Line 48, after "carried" insert -- out --
Line 36, "0.4M" should read -- 0.4 M --;
Line 54, "50° C." should read -- 50°C --; and "55° C." should read -- 55°C --; and "60° C." should read -- 60°C --; and "65° C." should read -- 65°C --;
Line 55, "72° C." should read -- 72°C --.

Column 7,
Line 3, "50° C." should read -- 50°C --; and "55° C." should read -- 55° C --; and "60° C." should read -- 60° C. --; and "65° C." should read -- 65° C --.
Line 27, "60° C." should read -- 60° C --.

Column 8,
Line 25, "USA" should read -- *USA* --.

Column 35,
Line 41, "60° C.;" should read -- 60°C; --;
Line 67, "72° C." should read -- 72° C. --.

UNITED STATES PATENT AND TRADEMARK OFFICE
CERTIFICATE OF CORRECTION

PATENT NO.   : 5,882,856
DATED        : March 16, 1999
INVENTOR(S)  : Anthony P. Shuber It is certified that error appears in the above-identified patent and that said Letters Patent is hereby corrected as shown below:

Column 36,
Line 33, GCGGTCCCAAAAGGTCAGT" should read -- GCGGTCCCAAAAGGGTCAGT --;
Line 53, "reannealling" should read -- reannealing --.

Column 38,
Line 33, "signal" should read -- single --.

Column 39,
Line 17, "DNA sequences free" should read -- DNA free --.

Signed and Sealed this

Twenty-first Day of May, 2002

*Attest:*

*Attesting Officer*

JAMES E. ROGAN
*Director of the United States Patent and Trademark Office*